(12) United States Patent
Carson

(10) Patent No.: US 6,375,674 B1
(45) Date of Patent: Apr. 23, 2002

(54) COOLING/HEATING PAD AND SYSTEM

(75) Inventor: Gary Allen Carson, Golden, CO (US)

(73) Assignee: Medivance, Inc., Louisville, CO (US)

( * ) Notice: Subject to any disclaimer, the term of this patent is extended or adjusted under 35 U.S.C. 154(b) by 0 days.

(21) Appl. No.: 09/476,850

(22) Filed: Jan. 3, 2000

Related U.S. Application Data

(63) Continuation-in-part of application No. 09/225,070, filed on Jan. 4, 1999, now Pat. No. 6,197,045.

(51) Int. Cl.[7] ............................................ A61F 7/00
(52) U.S. Cl. ........................ 607/104; 607/114; 5/422
(58) Field of Search ........................... 607/104, 114; 5/422, 423, 680, 736, 724

(56) References Cited

U.S. PATENT DOCUMENTS

| | | | |
|---|---|---|---|
| 2,250,325 A | 7/1941 | Barnes | 257/12 |
| 2,573,791 A | 11/1951 | Howells | 128/82.1 |
| 2,726,658 A | 12/1955 | Chessey | 128/400 |
| 3,088,288 A | 5/1963 | Elfving | 62/3 |
| 3,091,242 A | 5/1963 | Johnson, Jr. et al. | 128/402 |
| 3,463,161 A | 8/1969 | Andrassy | 128/402 |
| 3,674,019 A | * 7/1972 | Grant | 128/33 |
| 3,738,372 A | 6/1973 | Shioshvili | 128/400 |
| 3,757,362 A | 9/1973 | Bowlin et al. | 5/348 |
| 3,952,735 A | 4/1976 | Wirtschafter et al. | 128/163 |
| 4,098,279 A | * 7/1978 | Golden | 128/400 |
| 4,108,146 A | * 8/1978 | Golden | 128/400 |
| 4,118,946 A | 10/1978 | Tubin | 62/514 |
| 4,132,262 A | 1/1979 | Wibell | 165/26 |
| 4,154,245 A | 5/1979 | Daily | 128/400 |
| 4,170,998 A | 10/1979 | Sauder | 128/400 |
| 4,259,961 A | 4/1981 | Hood, III | 128/400 |
| 4,335,726 A | 6/1982 | Kolstedt | 128/400 |
| 4,338,944 A | 7/1982 | Arkans | 128/400 |
| 4,517,972 A | 5/1985 | Finch, Jr. | 128/156 |
| 4,572,188 A | 2/1986 | Augustine et al. | 128/380 |
| 4,919,134 A | 4/1990 | Streeter | 128/400 |
| 4,930,317 A | 6/1990 | Klein | 62/3.3 |
| 4,962,761 A | * 10/1990 | Golden | 128/400 |
| 5,097,829 A | 3/1992 | Quisenberry | 128/400 |
| 5,106,373 A | 4/1992 | Augustine et al. | 604/113 |
| 5,150,706 A | 9/1992 | Cox et al. | 128/400 |

(List continued on next page.)

Primary Examiner—Linda C. M. Dvorak
Assistant Examiner—Jocelyn Ram
(74) Attorney, Agent, or Firm—Marsh, Fischmann & Breyfogle, LLP

(57) ABSTRACT

A medical pad 10 includes a thermal exchange layer capable of absorbing and/or releasing heat to a patient and an adhesive surface 16A disposed on a skin-contacting side of the thermal exchange layer for adhering the pad 10 to the skin of the patient. The thermal exchange layer may comprise a fluid containing layer 12 for containing a thermal exchange fluid 14 capable of absorbing thermal energy from and/or releasing thermal energy to the patient. The pad 10 may also include a conformable, thermally conductive layer 16 between the adhesive surface 16A and the fluid containing layer 12 and an insulating layer 18 on the non-skin contacting side of the fluid containing layer 12. In some arrangements, transverse members 24, 26 or dimples 624 on insulating base member 618 are provided to define tortuous fluid passageways in fluid containing layer 12. A fluid circulating system 40 including a pump 42 connected downstream from a fluid outlet 22 and a fluid reservoir 44 connected upstream from a fluid inlet 20 may be employed to circulate the fluid 14 though the fluid containing layer 12. The fluid 14 is drawn from a reservoir 44 into the fluid containing layer 12 through the inlet 20 and out of the fluid containing layer 12 through the outlet 22 under negative pressure by the pump 42. When the pad 10 is adhered by the adhesive surface 16A to the skin of the patient, thermal energy is exchangeable between the patient and the fluid 14 circulated within the fluid containing layer 14 to cool and/or warm the patient.

25 Claims, 11 Drawing Sheets

U.S. PATENT DOCUMENTS

| | | | |
|---|---|---|---|
| 5,165,127 A | 11/1992 | Nicholson | 5/421 |
| 5,165,400 A | 11/1992 | Berke | 128/400 |
| 5,184,612 A | 2/1993 | Augustine | 128/400 |
| 5,300,101 A | 4/1994 | Augustine et al. | 607/107 |
| 5,300,102 A | 4/1994 | Augustine et al. | 607/107 |
| 5,304,213 A | 4/1994 | Berke et al. | 607/104 |
| 5,324,320 A | 6/1994 | Augustine et al. | 607/107 |
| 5,336,250 A | 8/1994 | Augustine | 607/107 |
| 5,344,436 A | 9/1994 | Fontenot et al. | 607/104 |
| 5,350,417 A | 9/1994 | Augustine | 607/104 |
| 5,360,439 A | 11/1994 | Dickerhoff et al. | 607/104 |
| 5,383,919 A | 1/1995 | Kelly et al. | 607/104 |
| 5,405,371 A | 4/1995 | Augustine et al. | 607/107 |
| 5,456,701 A | 10/1995 | Stout | 607/104 |
| 5,486,204 A | 1/1996 | Clifton | 607/96 |
| 5,486,207 A | 1/1996 | Mahawili | 607/104 |
| 5,514,169 A | 5/1996 | Dickerhoff et al. | 607/107 |
| 5,545,194 A | 8/1996 | Augustine | 607/104 |
| 5,591,220 A | 1/1997 | Mahawili | 607/104 |
| 5,609,620 A | 3/1997 | Daily | 607/105 |
| 5,632,769 A | 5/1997 | Kappel et al. | 607/104 |
| 5,640,728 A * | 6/1997 | Graebe | 5/606 |
| 5,643,139 A * | 7/1997 | Stout et al. | 482/14 |
| 5,643,337 A | 7/1997 | Kappel et al. | 607/107 |
| 5,658,325 A | 8/1997 | Augustine | 607/107 |
| 5,683,438 A | 11/1997 | Grahn | 607/104 |
| 5,693,079 A | 12/1997 | Van Duren | 607/104 |
| 5,697,963 A | 12/1997 | Augustine | 607/108 |
| 5,711,155 A | 1/1998 | DeVilbiss et al. | 62/3.7 |
| 5,720,773 A | 2/1998 | Lopez-Claros | 607/96 |
| 5,733,318 A | 3/1998 | Augustine | 607/104 |
| 5,735,890 A | 4/1998 | Kappel et al. | 607/104 |
| 5,749,109 A | 5/1998 | Kappel | 5/423 |
| 5,849,029 A | 12/1998 | Eckhouse et al. | 607/104 |
| 5,862,675 A | 1/1999 | Scaringe et al. | 62/193.3 |
| 5,871,526 A | 2/1999 | Gibbs et al. | 607/104 |
| 5,879,378 A | 3/1999 | Usui | 607/96 |
| 5,887,437 A | 3/1999 | Maxim | 62/4 |
| 5,913,849 A | 6/1999 | Sundstrom et al. | 604/291 |

* cited by examiner

COOLING/HEATING PAD AND SYSTEM

RELATED APPLICATION

This patent application is a continuation-in-part of U.S. patent application Ser. No. 09/225,070, filed Jan. 4, 1999 U.S. Pat. No. 6,197,045, Mar. 6, 2001, which is hereby incorporated by reference in its entirety.

FIELD OF THE INVENTION

The present invention generally relates to a medical pad and related system for cooling and/or heating a patient via contact thermal exchange. The present invention is particularly apt for treating stroke and head trauma patients.

BACKGROUND OF THE INVENTION

Medical pad systems for systemic cooling and/or heating of patients are known. Typically such systems include a pad that is placed on the patient. For example, the pad might be placed on the patient's torso. A fluid, such as water or air, is then circulated through the pad. Thermal energy is exchanged between the patient and the circulated fluid to cool or heat the patient. For example, water or air at an appropriate temperature below the desired temperature of the patient may be circulated through the pad to absorb heat from the patient and thereby achieve systemic cooling.

The therapeutic use of systemic cooling for a variety of conditions has been investigated. Of particular interest, it has recently been discovered that rapid systemic cooling of stroke and head trauma patients may have significant therapeutic benefits. Stroke is a major cause of death and neurological disability. Recent research suggests that even though a stroke victim's brain cells may lose their ability to function, the cells do not necessarily die quickly. In fact, brain damage from a stroke may take hours to reach maximum effect. Neurologic damage may be limited and the stroke victim's outcome improved if a neuroprotectant therapy is applied within this time frame. As a result of vehicle crashes, falls and the like, many people suffer traumatic brain injury (e.g. impairment of cognitive abilities or physical functioning). Elements in the genesis of traumatic brain injury are now understood to overlap with elements in the genesis of neurologic damage in stroke victims. Delayed secondary injury at the cellular level after the initial head trauma event is now recognized as a major contributing factor to the ultimate tissue loss that occurs after brain injury.

One neuroprotectant therapy that may be applied early in the treatment process to stabilize and reduce ongoing cellular damage is hypothermia. Studies have shown that treatment with mild hypothermia, defined as lowering core body temperature 2–3° C., confers neuroprotection in stroke victims, and may hasten neurologic recovery and improve outcomes when applied for twenty-four to seventy-two hours in cases of traumatic brain injury.

SUMMARY OF THE INVENTION

In view of the foregoing, one object of the present invention is to provide an improved medical pad and related system that can be employed to lower a patient's body temperature rapidly and accurately.

Another object of the present invention is to provide an improved medical pad and related system that can be employed to maintain a patient in a state of mild hypothermia for an extended period.

A further object of the present invention is to provide an improved medical pad and related system that can be employed to raise a patient's body temperature in a controlled manner.

Yet another object of the present invention is to provide an improved medical pad that yields enhanced interface with a patient's skin.

These and other objectives and advantages are achieved by various aspects of the present invention. According to one aspect of the present invention, a medical pad for contacting and exchanging thermal energy with a patient includes a thermal exchange layer capable of absorbing and/or releasing heat from/to a patient, and an adhesive surface disposed on a skin-contacting side of the thermal exchange layer for adhering the pad to the skin of the patient. The thermal exchange layer may comprise a fluid containing layer for containing a thermal exchange fluid capable of absorbing thermal energy from and/or releasing thermal energy to the patient. The thermal exchange fluid, which may be a liquid (e.g. water) or a gas, may be circulated within the fluid containing layer from a fluid inlet to a fluid outlet.

The fluid may be circulated by drawing fluid into the fluid containing layer through the inlet and out of the fluid containing layer through the outlet under negative pressure by a pump connected downstream from the outlet. The fluid containing layer may be defined by a pair of correspondingly sized sections of a nonporous material that are welded to one another along perimeter edges thereof to form a waterproof seal. When the pad is adhered by the adhesive surface to the skin of the patient, thermal energy is exchangeable between the patient and the fluid circulated within the fluid containing layer. In this regard, the pad may be utilized in cooling and/or heating procedures depending upon the relative temperature of a patient and the fluid circulated within the fluid containing layer. As one alternative to fluid circulation, the thermal exchange layer may include electrically resistive elements therein for generating thermal energy that is transferable from the pad to the patient.

According to a further aspect of the present invention, flow path defining means may be disposed within a fluid containing layer of an improved medical pad. The flow path defining means define one or more tortuous fluid flow paths from the inlet to the outlet in each of at least two flow path layers within the fluid containing layer. The tortuous fluid flow paths inhibit the formation of boundary layers along the inside surfaces of the fluid containing layer. The flow path defining means may comprise a first plurality of elongated members that are arranged in a first layer and oriented in a first direction and a second plurality of elongated members that are arranged in a second layer and oriented in a second direction that is transverse to the first direction (e.g. to define a cross-hatch pattern). The first plurality of elongated members may be arranged within the first layer in a parallel fashion and the second plurality of elongated members may be arranged in the second layer in a parallel fashion. The two layers of elongated members may be defined by a netting material. A fluid inlet and outlet may be provided in the pad and each port may include a fluid flow port that is oriented for fluid flow therethrough in a direction that is transverse to the first and second directions of orientation of the elongated members.

According to an additional aspect of the present invention, a conformable, thermally conductive layer is disposed between an adhesive surface and fluid containing layer of a medical pad. The conformable, thermally conductive layer is sufficiently thick and is comprised of a sufficiently conformable material so as to conform to the contours of a patient's skin and envelop skin hair. As a result, insulating air pockets between the pad and the skin of a patient are reduced. In this regard, the conformable, thermally conductive layer is preferably at least about 0.013 cm thick and is preferably comprised of a material having an elastic modulus of between about 40 and 1000 pascals. The conformable, thermally conductive layer also provides for sufficient thermal exchange therethrough between the skin of the patient and the thermal exchange layer. In this regard, the conformable, thermally conductive layer is preferably less than about 0.15 cm thick and is preferably comprised of a material having a coefficient of thermal conductivity of at least about 2.00 cal/hr-cm-° C. so that the conformable, thermally conductive layer preferably has a minimum thermal transfer rate of at least about 13.33 cal/hr-cm$^2$-° C. The conformable, thermally conductive layer may comprise a first material, such as a liquid (e.g. water), suspended in a matrix defined by a second material, such as a polymer. In this regard, the liquid preferably comprises between about 30 to 95 percent by weight of the total weight of the first and second materials. The adhesive surface and thermal transfer layers in the noted arrangements may be separately comprised of distinct materials. Alternatively, a thermally conductive layer may be comprised of a hydrogel material having sufficient adhesive properties so as to integrally provide the adhesive surface. In any case, the adhesive surface should have sufficient adhesive strength to hold the pad in place yet not cause tissue damage when removed. In this regard, the adhesive surface could preferably have a peel value against skin at initial application of at least about 10 gm/inch.

According to yet another aspect of the present invention, an insulating layer may be disposed on the non-skin contacting side of a fluid containing layer of a medical pad. The insulating layer inhibits heat transfer between the surrounding air and the fluid circulated through the fluid containing layer thereby enhancing the efficiency of the pad. Preferably, the insulating layer is comprised of a material having a coefficient of thermal conductivity of less than 1.00 cal/hr-cm-° C. and is preferably at least about 0.06 cm thick so that the insulating layer preferably has a maximum thermal transfer rate of about 16.67 cal/hr-cm$^2$-° C.

In a related aspect of the invention, a dual function layer may be utilized to provide one side of a fluid containing layer of a medical pad, as well as flow path defining means within the fluid containing layer. More particularly, a flexible, insulating material (e.g., a non-permeable polymer or polymer, closed-cell foam) may be fabricated into a base member having a plurality of integrally defined dimples projecting from a base portion, wherein the base member and a flexible, non-permeable film or sheet (as described above) may be interconnected to define a fluid containing layer therebetween, with the dimples both supporting the flexible sheet and defining internal fluid flow pathways. In turn, a conformable, thermally conductive layer (e.g., as described above) may be laminated to the flexible sheet. An adhesive surface (e.g., as described above) may be disposed on the outward, or skin-facing, side of the thermally conductive layer. Preferably, the base member may function as an insulating layer (e.g., as described above) and may have a density of between about 2 to 12 lb/ft$^3$. By way of primary example, the base member may comprise at least one material selected from a group consisting of: polyethylene, polyurethane, polyvinyl chloride, and ethylene-vinyl acetate copolymers. The dimples may be provided in a variety of configurations and patterns, including cylindrical or truncated cones arranged in rows/columns so that adjacent rows and adjacent columns are offset from each other by 60°. In another arrangement, elongated, truncated, pyramidal dimples may be disposed in a herringbone pattern. Preferably, the dimples will have a height of between about 0.02 and 0.2 inches, and most preferably, between about 0.04 and 0.1 inches. One or more ribbing members may be positioned between adjacent ones of the dimples (e.g., via integral molding as part of the base member) to extend across the fluid containing layer in the direction of desired fluid flow from a fluid inlet edge to a fluid outlet edge.

It should be appreciated that several features of a pad embodiment constructed in accordance with the present invention facilitate efficient thermal transfer between the pad and the patient. For example, overall construction of the pad may be relatively thin since it is preferably operated under negative pressure. The use of a cross hatched layer of netting material within or a dual function layer with dimples to partially define the fluid containing layer facilitates a high rate of thermal transfer under negative pressure within the fluid containing layer, and further allows fluid which has absorbed/released thermal energy from/to the patient to be rapidly cycled. Because the pad may be relatively thin, it is conformable. The conformable nature of the pad, and in particular, the conformable, thermally conductive layer, permits enhanced direct contact between the pad and the patient thereby enhancing the effective area of thermal exchange between the pad and the patient. An adhesive surface particularly assures direct contact between the patient's skin and the pad.

According to yet another aspect of the present invention, a method of exchanging thermal energy between a patient and a medical pad includes contacting the external surface of the pad with the skin of the patient in order to establish a thermal interface between the skin of the patient and the pad. A thermal exchange fluid reservoir is interconnected with a fluid inlet to the fluid containing layer. The reservoir contains a thermal exchange fluid that is capable of absorbing and/or releasing thermal energy. A pump is coupled with an outlet from the fluid containing layer. The pump is operated to establish negative pressure at the outlet and thereby draw fluid from the reservoir though the inlet into the fluid containing layer and out through the outlet.

According to related aspects of the inventive method, in the step of contacting, the pad may be adhered to the patient by bringing an adhesive surface disposed on the skin contacting side of the fluid containing layer into contact with the patient. In the step of operating the pump, the body temperature of the patient may be monitored and the pump may be operated so as to change the patient's body temperature a predetermined amount. For example, the method of the present invention may be employed to quickly reduce the body temperature of stroke and head trauma patients about 2–3° C. Further, in the step of operating, the fluid may be drawn through the fluid containing layer along one or more tortuous fluid flow paths defined by first and second pluralities of elongated members within the fluid containing layer or by dimples comprising a dual function backing layer. Additionally, the method of the present invention may include utilizing a conformable, thermally conductive layer between the fluid containing layer and the patient to enhance the thermal energy exchange as well as insulating the pad with a layer of insulating material disposed on the non-skin contacting side of the fluid containing layer to thereby inhibit transfer of thermal energy between the fluid circulated within the fluid containing layer and the surrounding air. As noted, the insulating layer may define the backside of the fluid containing layer as well as fluid flow pathways therewithin (e.g., via the use of dimples as noted above).

These and other aspects and related advantages of the present invention should become apparent from a review of the following detailed description when taken in conjunction with the accompanying figures.

DETAILED DESCRIPTION

Figure 1:
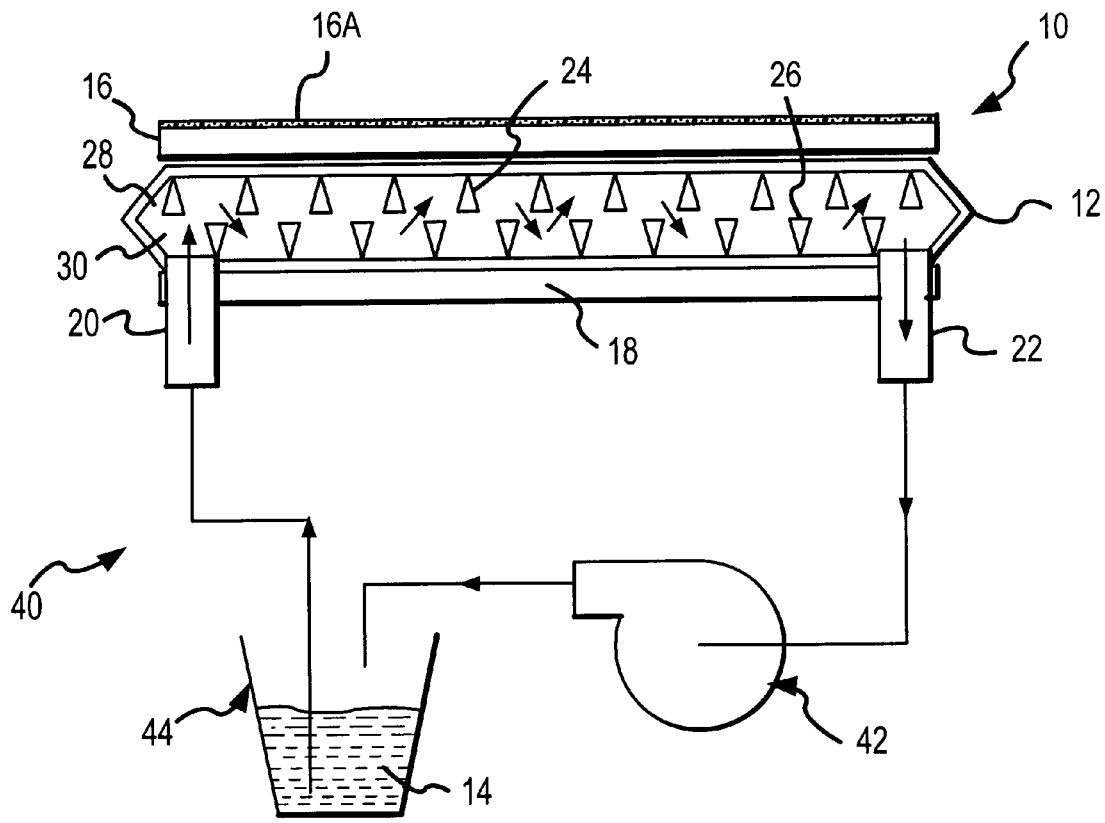
FIG. 1 illustrates a schematic diagram of one embodiment of a medical pad and related fluid circulating system in accordance with the present invention.

Referring now to FIG. 1, there is shown one embodiment of a medical pad 10 in accordance with the present invention. The pad 10 includes a thermal exchange layer that is capable of absorbing and/or releasing thermal energy. In the illustrated embodiment, the thermal exchange layer comprises a fluid containing layer 12 for containing a thermal exchange fluid 14 that is capable of absorbing and/or releasing thermal energy. However, in other embodiments the thermal exchange layer may include electrically resistant elements that may generate thermal energy to be released by the pad 10.

Referring again to the illustrated embodiment in FIG. 1, the fluid 14 may be a liquid such as water, or it may be a gas. A conformable, thermally conductive layer 16 is disposed on a skin contacting side (the upper side in FIG. 1) of the fluid containing layer 12, and an insulating layer 18 is disposed on a non-skin contacting side (the lower side in FIG. 1) of the fluid containing layer 12. The pad 10 also includes a fluid inlet 20 and a fluid outlet 22 for permitting fluid flow into and out of the fluid containing layer 12, respectively. An adhesive surface 16A is disposed on the skin contacting side of the conformable, thermally conductive layer 16 for adhering the pad 10 to the skin of a patient. While not shown in FIG. 1, a removable release liner may be provided over the adhesive surface 16A to protect the adhesive surface 16A from contamination while the pad 10 is not in use. The release liner may be selectively removed when the pad 10 is used. A first plurality of elongated members 24 are arranged in a first layer and a second plurality of elongated members 26 are arranged in a second layer within the fluid containing layer 12. Together, the first and second pluralities of elongated members 24, 26 define one or more tortuous fluid flow paths in first and second flow path layers 28, 30 within the fluid containing layer 12 from the inlet 20 to the outlet 22.

In FIG. 1, the medical pad 10 is depicted with an exemplary fluid circulating system 40. The exemplary fluid circulating system 40 includes a pump 42 that is a connected downstream from the fluid outlet 22 and a fluid reservoir 44 connected upstream from the inlet 20. The fluid 14 is circulateable within the fluid circulating system 40 and the fluid containing layer 12 along the tortuous fluid flow path from the inlet 20 to the outlet 22 as represented by the arrows in FIG. 1. The fluid 14 is drawn under negative pressure by the pump 42 from the reservoir 44 through the fluid containing layer 12 and returned the reservoir 44. As the fluid 14 is drawn through the fluid circulating layer, thermal energy is exchanged between the patient and the fluid 14. For example, if the fluid 14 is cooler than the patient, heat from the patient will be absorbed by the fluid 14 thereby cooling the patient. Alternatively, if the fluid 14 is warmer than the patient, heat from the fluid 14 will be absorbed by the patient thereby warming the patient.

Figure 2:
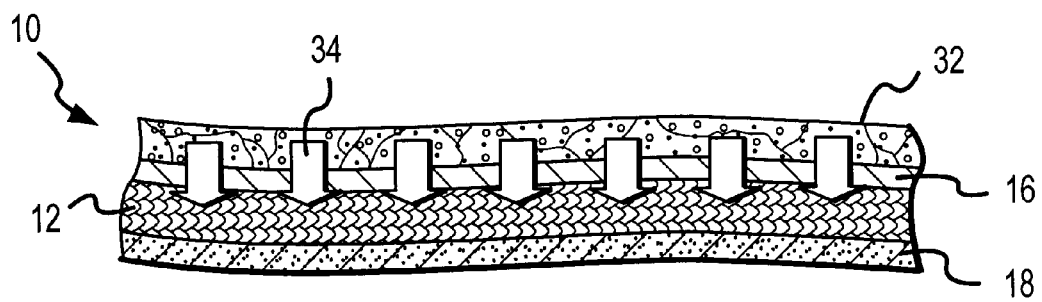
FIG. 2 illustrates a schematic view showing heat transfer between a patient and a medical pad in accordance with the present invention.

Referring now to FIG. 2, an example of the heat transfer process that occurs while cooling a patient with the medical pad 10 is shown. The pad 10 is in contact with the skin 32 of a patient and fluid 14 at an appropriate temperature below that of the patient is circulated through the fluid containing layer 12. Heat (represented by the arrows 34) is transferred from the patient's skin 32 through the conformable, thermally conductive layer 16 to the fluid 14 circulated in the fluid containing layer 12. The insulating layer 18 on the non-skin contacting side of the pad 10 inhibits heat transfer from the surrounding air thereby enhancing the amount of heat transfer 34 from the skin 32. Because the pad 10 of the present invention is flexible and is operated under negative pressure, it substantially conforms to the contours of the portion of the patient with which it is in contact. Further, by adhering to the skin 32, the adhesive surface 16A helps maintain the conformance of the pad 10 to the patient's contours and restricts unintentional movement of the pad 10. The substantial conformance of the pad 10 to the contours of the patient inhibits the existence of insulating air pockets between the patient's skin 32 and the pad 10 and maximizes the surface area of the skin 32 that is in close proximity with the fluid 14 circulated through the fluid containing layer 12. The limited existence of air pockets and maximal skin 32 surface in close proximity with the circulated fluid 14 enhances the efficiency of the heat transfer process because heat transfer 34 may occur over substantially all of the skin contacting side of the pad 10. As will be appreciated, this is in contrast with a medical pad having a corrugated geometry which may reduce the effective area of heat transfer.

Figure 3:
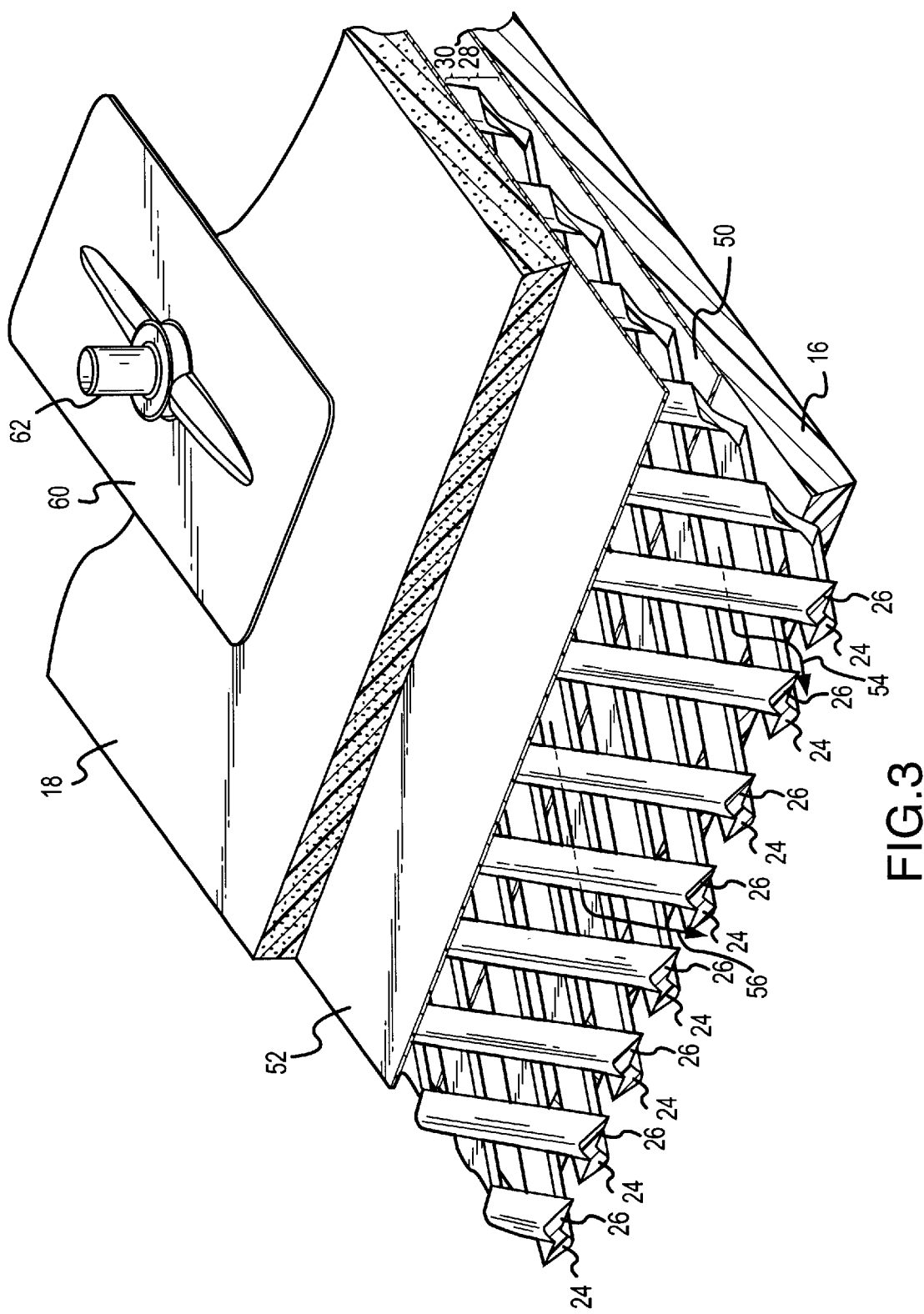
FIG. 3 illustrates a partial cut-away perspective view of the medical pad depicted in FIG. 1.

Referring now to FIG. 3, a portion of the pad 10 is shown in greater detail. The fluid containing layer 12 may be defined by first and second sheets 50, 52 of a non-porous, thin flexible film material. The first and second sheets 50, 52 are correspondingly sized and welded to one another along perimeter edges thereof to form a waterproof seal. The sheets 50, 52 may be comprised of a polymer material such as polyurethane, polyvinyl chloride, polypropylene, or nylon. Preferably, the sheets 50, 52 are at least about 0.0010 inches thick, and, more preferably, they are between about 0.0015 and 0.0040 inches thick. The sheets 50, 52 may be shaped in a variety of corresponding configurations to produce pads in a plurality of shapes for localized application on various body portions of a patient. For example, the sheets 50, 52 may be configured to produce a pad specifically configured for application on a patient's torso, neck, feet, arm, or thighs.

The first and second pluralities of elongated members 24, 26 are disposed between the first and second sheets 50, 52. As can be seen in FIG. 3, the first plurality of elongated members 24 are arranged in a first layer and generally oriented in a first direction. Further, the first plurality of elongated members 24 may be arranged in a parallel fashion. The second plurality of elongated members 26 are arranged in a second layer and generally oriented in a second direction transverse to the first direction so that the first and second members 24, 26 form a crisscrossed configuration. Further, the second plurality of elongated members 26 may also be arranged in a parallel fashion.

Together, the first and second plurality of elongated members 24, 26 define a plurality of tortuous fluid flow paths in the first and second layers 28, 30. For example, fluid 14 may follow the tortuous path shown by arrow 54 in FIG. 3, wherein fluid 14 flows in the first layer 28 in the first direction between adjacent first elongated members 24 and between one of the second elongated members 26 and the first sheet 50. The fluid 14 then flows from the first layer 28 to the second layer 30. It then flows in the second layer 30 in the second direction between adjacent second elongated members 26 and between one of the first elongated members 24 and the second sheet 52. The fluid 14 returns from the second layer 30 to the first layer 28 where it again flows in the first direction between adjacent first elongated members 24 and between one of the second elongated members 26 and the first sheet 50. Another possible tortuous fluid flow path is represented by arrow 56 in FIG. 3. The fluid 14 flows in the first layer 28 in the first direction between adjacent first elongated members 24. After flowing between several of the second elongated members 26 and the first sheet 50, the fluid 14 then flows from the first layer 28 to the second layer 30 (e.g. when it reaches the perimeter of the pad 10). The fluid 14 then flows in the second direction between adjacent second elongated members 30 and between several first elongated members 28 and the second sheet 52. It should be appreciated that tortuous fluid flow paths other than the ones represented by arrows 54, 56 may also be defined by the first and second pluralities of elongated members 24, 26.

The tortuous fluid flow paths inhibit the formation of boundary layers wherein some of the fluid 14 remains substantially stationary along the inside surfaces of the fluid containing layer 12 while the remaining fluid 14 flows from the inlet 20 to the outlet 22. Such boundary layers may reduce the efficiency of the pad 10 because fluid 14 which can no longer absorb additional heat (if the pad is being used to a cool a patient) remains within the fluid containing layer 12. Furthermore, the crisscrossed geometry of the layers of first and second elongated members 24, 26 also facilitates an even, low pressure drop between the inlet 20 and the outlet 22 required by a negative flow pressure circulating system 40.

In addition to defining a tortuous fluid flow path, the first and second pluralities of elongated members 24, 26 keep the first and second sheets 50, 52 spaced apart from one another (except along the perimeter edges where they are welded), preventing the first and second sheets 50, 52 from collapsing toward one another restricting flow in the fluid containing layer 12. In this regard, each of the first and second elongated members 24, 26 may have a triangular cross-sectional configuration as is shown in FIG. 3. Facing sides of the first and second pluralities of elongated members 24, 26 are preferably welded to one another where the members cross. Each of the first and second elongated members 24, 26 are also preferably welded to the first and second sheets 50, 52 along respective edges in contact with the inner surfaces of the sheets 50, 52.

The two layers of first and second pluralities of elongated members 24, 26 may be defined by one layer of extruded netting material such as that produced by Nalle Plastics, Inc. of Austin, Tex. The netting should be sufficiently thick so as to allow for fluid flow between the elongated members 24, 26 but not too thick to permit shunting. Preferably, the netting (i.e the two layers of first and second elongated members 24, 26) has a thickness of at least about 0.010 inches, and more preferably, is between about 0.040 and 0.080 inches for a typical pad 10 covering 2 square feet. The netting is preferably comprised of a resin having a relatively low flexural modulus, such as an EVA/PE blend or one-hundred percent EVA. Although only one netting layer is depicted in FIG. 3, more than one layer of netting may be disposed between the sheets 50, 52 to achieve a more desirable combination of support between the sheets 50, 52 and low pressure drop fluid flow from the inlet 22 to the outlet 24.

The conformable thermally conductive layer 16 conforms to the contours of the skin of the patient and envelops skin hair thereby inhibiting the existence of insulating air pockets between the pad 10 and the patient's skin. Preferably, the conformable, thermally conductive layer is comprised of a material having an elastic modulus of between about 40 and 1000 pascals and is at least about 0.013 cm thick. The conformable, thermally conductive layer also permits sufficient thermal exchange therethrough between the skin of the patient and the thermal exchange layer. Preferably, the conformable, thermally conductive layer is less than about 0.15 cm thick and is comprised of a material having a coefficient of thermal conductivity of between about 2.00 and 5.00 cal/hr-cm-° C. so that the conformable, thermally conductive layer has a preferred thermal transfer rate between about 13.33 and 384.62 cal/hr-cm$^2$-° C. Most preferably, the conformable, thermally conductive layer is about 0.635 cm thick and is comprised of a material having a thermal conductivity coefficient of about 2.66 cal/hr-cm-° C. resulting in a thermal transfer rate of about 41.9 cal/hr-cm$^2$-° C.

The adhesive surface 16A on the conformable, thermally conductive layer 16 should be comprised of a material having sufficient adhesive strength for holding the pad 10 in place and maintaining thermal contact without having too great of an adhesive strength so as to cause tissue damage during removal. A material having a peel value against skin at initial application of between about 10 to 200 gm/inch is satisfactory. Most preferably, the peel value against skin at initial application is between about 20 to 80 gm/inch.

The conformable thermally conductive layer 16 may be comprised of a first material suspended in a matrix defined by a second material. The first material may be a liquid (e.g. water) and the second material may be a polymer. Preferably, the liquid comprises between about 30 to 95 percent by weight of the total weight of the first and second materials. The adhesive surface 16A may be comprised by the same material comprising the conformable, thermally conductive layer. For example, the conformable, thermally conductive layer and adhesive surface may be comprised of an adhesive cross-linked hydrogel material such as "Polyhesive" manufactured by Valleylab of Boulder, Colo. or such as is described in U.S. Pat. No. 5,645,855 to Lorenz. A hydrogel material is appropriate because its adhesive strength does not tend to increase over time as compared with traditional adhesive, it tends to envelop skin hair thereby facilitating good thermal contact, and its high water content results in relatively high thermal conductivity. Alternatively, the conformable, thermally conductive layer and adhesive surface may be comprised of different materials. For example, an appropriate adhesive material may be sprayed or otherwise applied onto the surface of a layer of an appropriate conformable thermally conductive material different than the adhesive material.

The insulating layer 18 insulates the non-skin contacting side of the pad 10 from the surrounding air. This inhibits thermal energy exchange between fluid 14 in the fluid containing layer 12 and the surrounding air thereby enhancing the efficiency of the pad 10. The insulating layer 18 preferably has a thermal transfer rate therethrough of between about 0.30 and 16.67 cal/hr-cm$^2$-° C. In this regard, the insulating layer is preferably between about 0.060 and 0.50 cm thick and is comprised of a material having a coefficient of thermal conductivity of between about 0.15 and 1.00 cm/hr-cm-° C. Most preferably, the insulating layer is about 0.152 cm thick and is comprised of a material having a thermal conductivity coefficient of about 0.31 cal/hr-cm-° C. providing the insulating layer with a thermal transfer rate of about 2.04 cal/hr-cm$^2$-° C. The insulating layer 18 is preferably comprised of closed cell foam and made from polyethylene resin, polyvinyl chloride or urethane. The foam may have an acrylic pressure sensitive adhesive, such as product number MED 416 from Avery Dennison, on one side for bonding the insulating layer 18 to the second sheet 52. In addition to insulating the non-skin contacting side of the pad 10, the closed cell foam inhibits air penetration that could lead to the formation of condensation.

Also shown in FIG. 3 is a plastic manifold 60. The manifold 60 is bonded by, for example, an adhesive to the insulating layer 18. The manifold 60 overlies an opening formed through the insulating layer 18 and second sheet 52. The opening permits fluid flow from inside the fluid containing layer 12 through a fluid flow port 62 formed in the manifold 60. As is shown in FIG. 3, the fluid flow port 62 is preferably oriented for fluid flow therethrough in a direction transverse to the first and second directions of orientation of the first and second elongated members 24, 26. Although only one manifold 60 is depicted in FIG. 3, it should be appreciated that the pad 10 includes two manifolds 60 generally located adjacent to respective opposing edges of the pad 10. The port 62 of one of the manifolds is connectable to the reservoir 44 so that the manifold functions as the fluid inlet 20. The port 62 of the other manifold 60 is connectable to the pump 42 so that the other manifold 60 functions as the fluid outlet 22.

Figure 4:
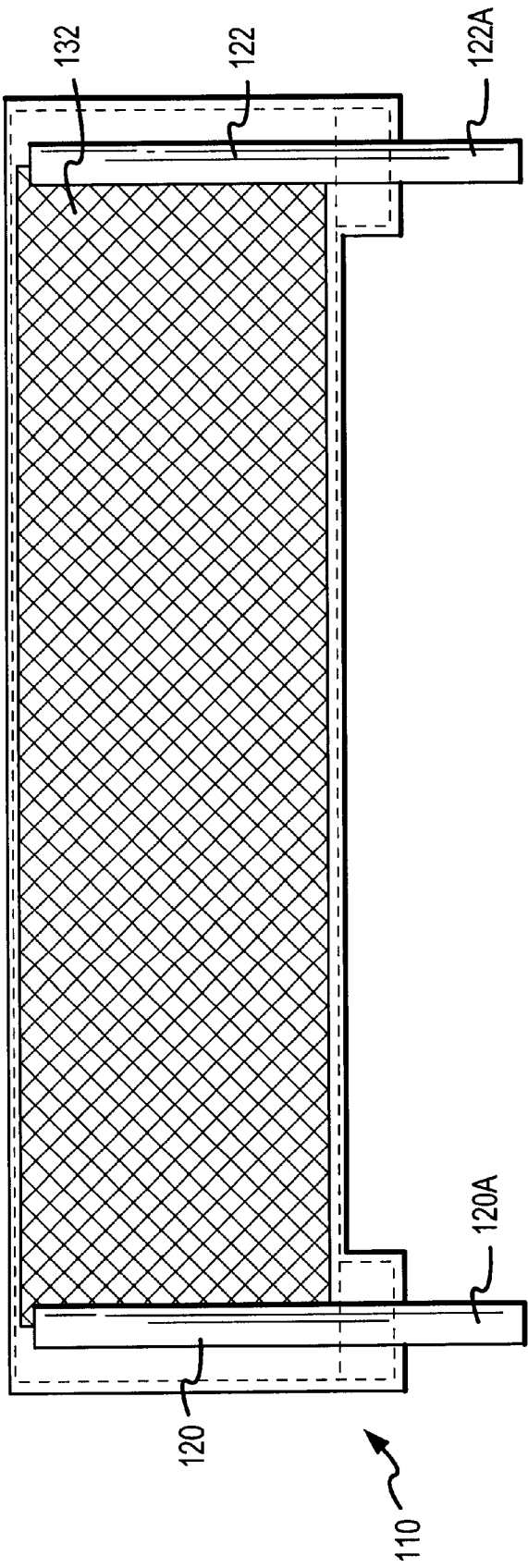
FIG. 4 illustrates a top view of another embodiment of a medical pad in accordance with the present invention.
Figure 5:
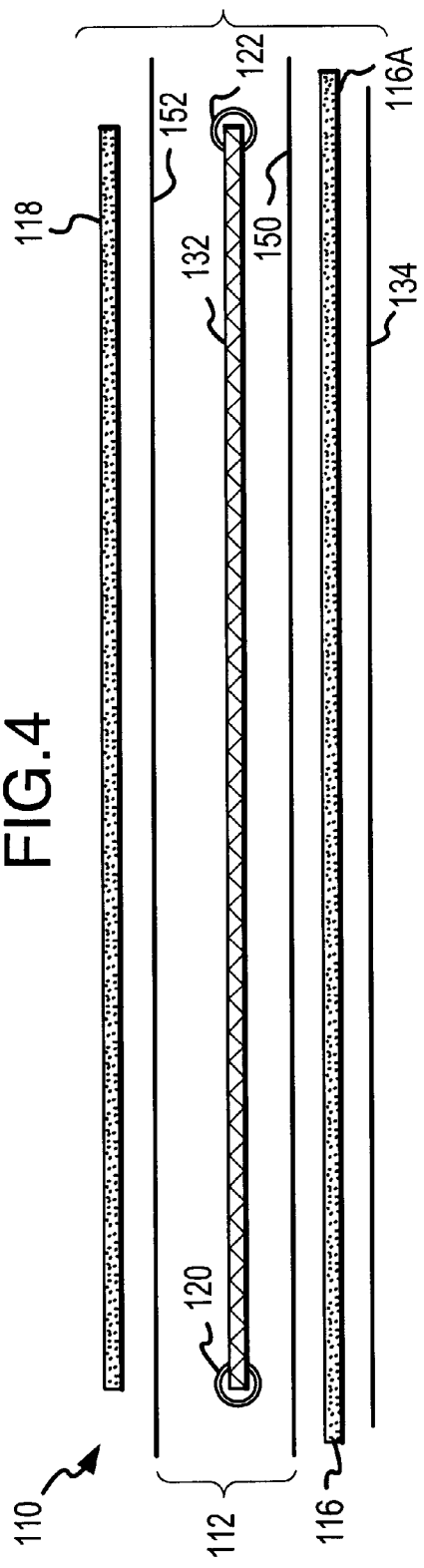
FIG. 5 illustrates an exploded side view of the medical pad depicted in FIG. 4.

Referring now to FIGS. 4–5, there is shown an alternative embodiment of a pad 110 in accordance with the present invention. The pad 110 includes first and second sheets 150, 152 that are welded to one another along perimeter edges thereof to define a fluid containing layer 112. A layer of extruded netting 132 is positioned in the fluid containing layer 112 between the first and second sheets 150, 152. The netting 132 may be comprised of first and second pluralities of elongated members arranged in first and second layers as described above in reference to FIG. 3. A conformable, thermally conductive layer 116 comprised of, for example, a hydrogel is disposed on a skin contacting side of the fluid containing layer 112. An adhesive surface 116A is disposed on the skin contacting side of the conformable, thermally conductive layer 116. A removable release liner 134 may be disposed over the adhesive surface 116A. The release liner 134 may be selectively removed when the pad 110 is used. An insulating layer 118 comprised of, for example, closed cell foam is disposed on the non-skin contacting side of the fluid containing layer 112. The pad 110 also includes a fluid inlet distribution tube 120 having an inlet port 120A and a fluid outlet distribution tube 122 having an outlet port 122A. The inlet and outlet distribution tubes 120, 122 are disposed adjacent to opposing edges of the pad 110 and extend into the fluid containing layer 112 parallel with the edge of the pad 110 to which they are adjacent. The inlet distribution tube 120 includes a slit extending longitudinally along a portion thereof for receiving the netting 132 and permitting the introduction of fluid which enters the tube 120 through the inlet port 120A into the fluid containing layer 112. The outlet distribution tube 122 also includes a slit extending longitudinally along a portion of the tube 122 for receiving the netting 132 and permitting the exit of fluid from the fluid containing layer 112 into the outlet tube 122 and out of the outlet port 122A.

Figure 6:
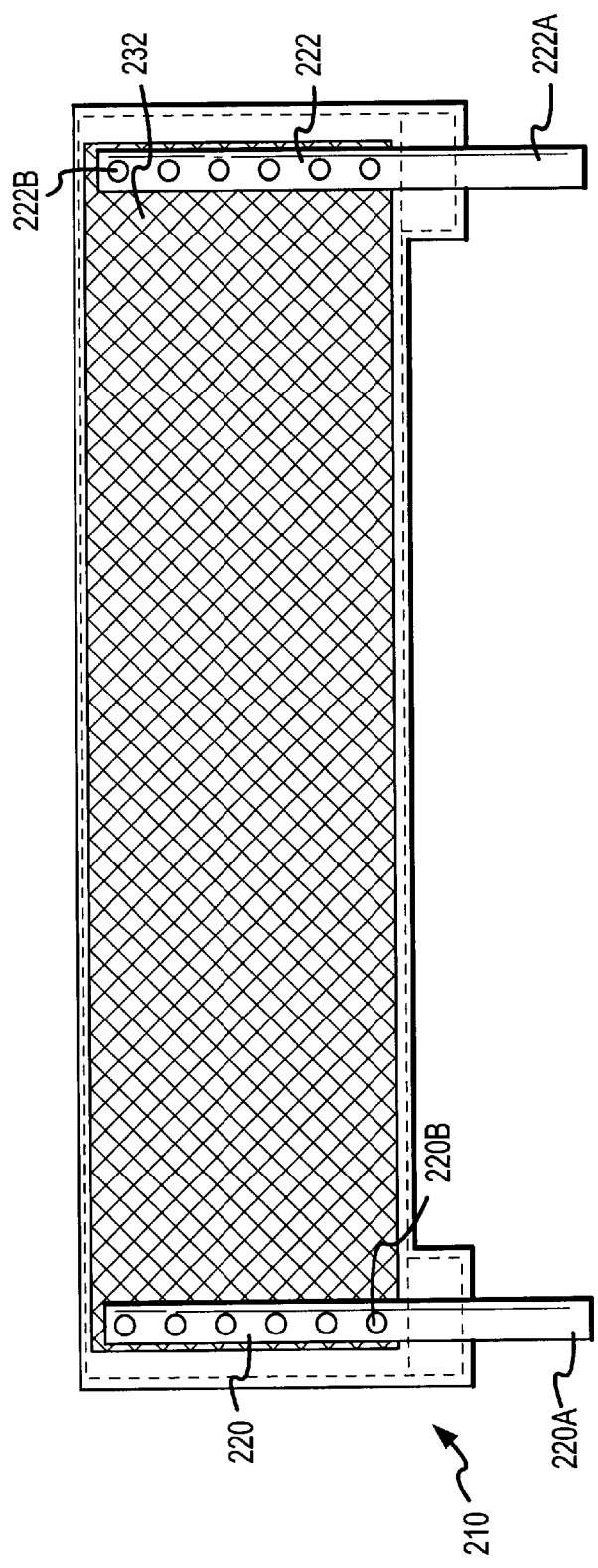
FIG. 6 illustrates a top view of a further embodiment of a medical pad in accordance with the present invention.
Figure 7:
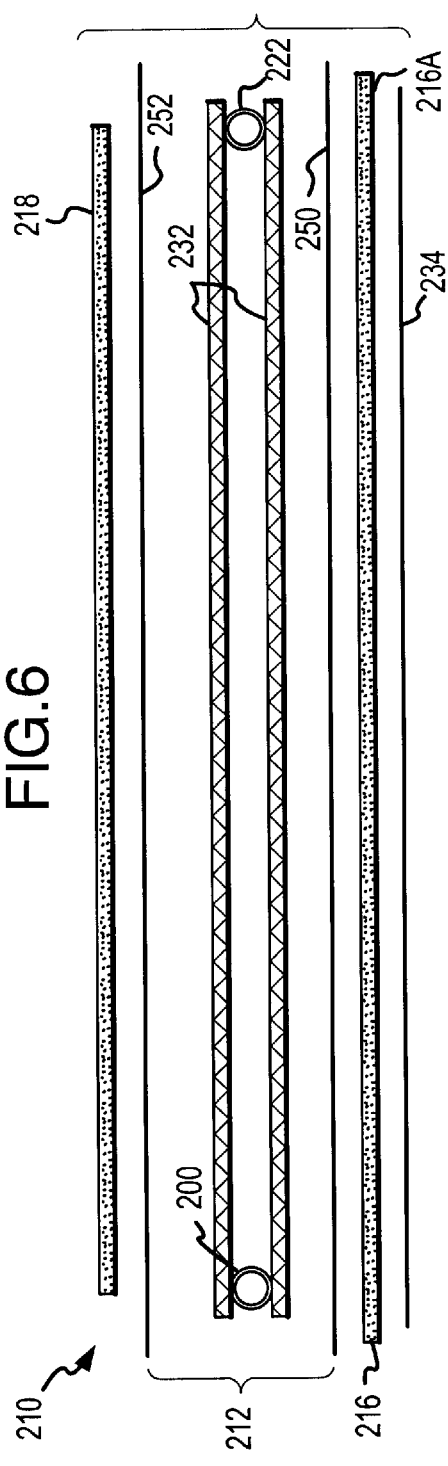
FIG. 7 illustrates an exploded side view of the medical pad depicted in FIG. 6.

Referring now to FIGS. 6–7, there is shown another embodiment of a medical pad 210 in accordance with the present invention. The pad 210 includes first and second sheets 250, 252 that are welded to one another along perimeter edges thereof to define a fluid containing layer 212. Two layers of extruded netting 232 are positioned in the fluid containing layer 212 between the first and second sheets 250, 252. Each layer of extruded netting may be comprised of first and second layers of elongated members as described above in reference to FIG. 3. A conformable, thermally conductive layer 216 comprised of, for example, a hydrogel is disposed on a skin contacting side of the fluid containing layer 212. An adhesive surface 216A is disposed on the skin contacting side of the conformable, thermally conductive layer 216. A removable release liner 234 may be disposed on the adhesive surface 216A of the conformable, thermally conductive layer 216. The release liner 234 may be selectively removed when the pad 210 is used. An insulating layer 218 comprised of, for example, closed cell foam is disposed on the non-skin contacting side of the fluid containing layer 212. The pad 210 also includes a fluid inlet distribution tube 220 having an inlet port 220A at one end thereof and a fluid outlet distribution tube 222 having an outlet port 222A at one end thereof. The inlet and outlet distribution tubes 220, 222 are disposed adjacent to opposing edges of the pad 210 and extend into the fluid containing layer 212 between the layers of extruded netting 232 and parallel with the edge of the pad 210 to which they are adjacent. Apertures 220B formed on opposing sides of the inlet distribution tube 220 permit fluid which enters the inlet distribution tube 220 through the inlet port 220A to flow into the fluid containing layer 212. Apertures 222B formed on opposing sides of the outlet distribution tube 222 permit fluid to flow from the fluid containing layer 212 into the outlet distribution tube 222 and out the outlet port 222A.

Figure 8:
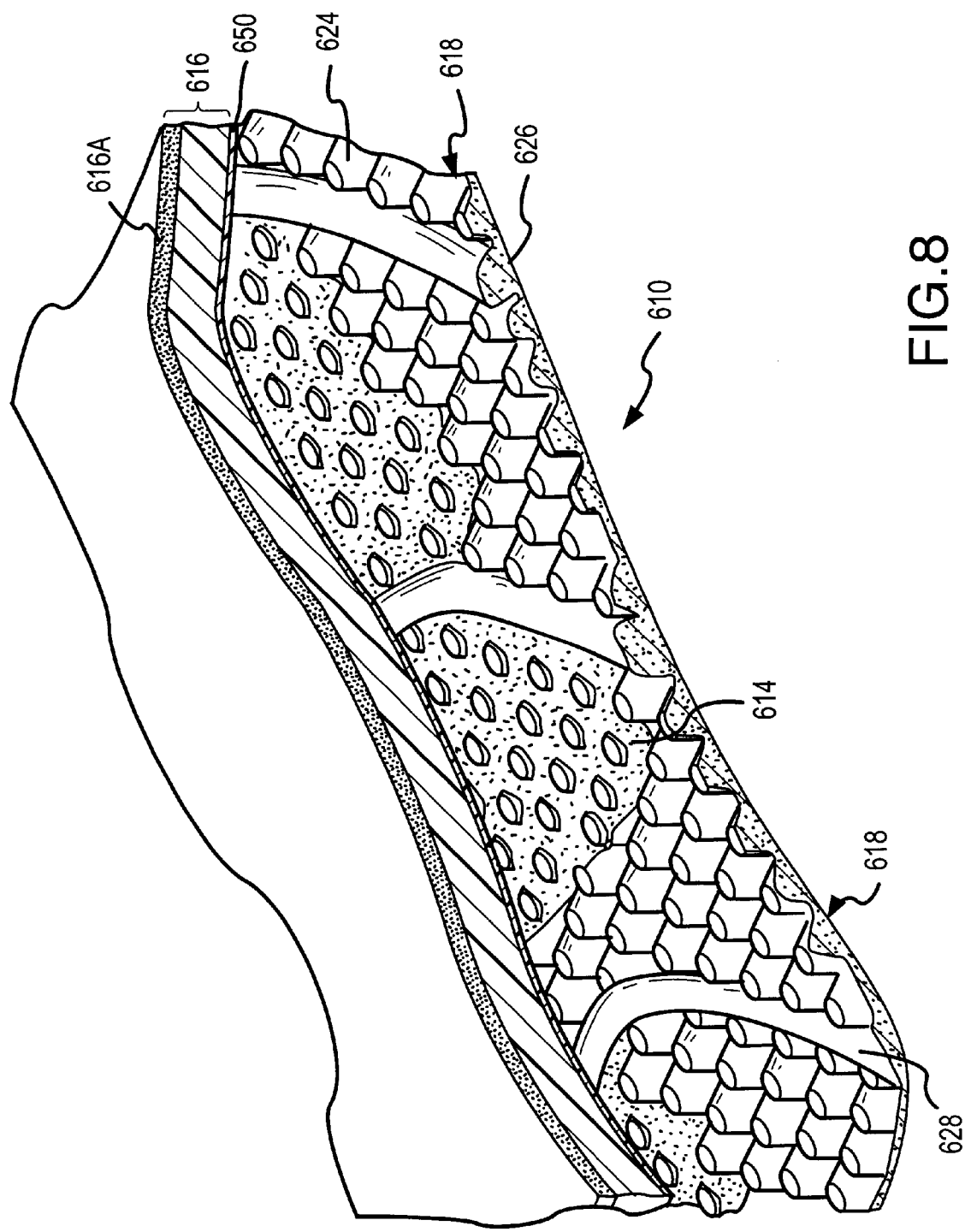
FIG. 8 illustrates a perspective, partial cut-away view of another embodiment of a medical pad in accordance with the present invention.

FIG. 8 illustrates a perspective, partial cut-away view of yet another embodiment of a medical pad 610 in accordance with the present invention. The pad 610 includes a base member 618 interconnected to a flexible sheet or film layer 650 (e.g., constructed as per sheet 50 described above) so as to define a fluid containing layer therebetween. As will be further described, base member 618 may be fabricated to provide a pattern of dimples 624 extending away from a back surface layer 626 so as to define fluid pathways between the dimples 624. Further, base 618 may be formed so as integrally define rib members 628 extending laterally (e.g., in a serpentine fashion) between adjacent dimples 624 to further establish the desired fluid flow across medical pad 610 (e.g., from a circulating fluid inlet edge to a circulating fluid outlet edge). In this regard, FIG. 8 illustrates the flow of a circulated fluid 614 through the pad 610 between rib members 628 and dimples 624. A conformable, thermally conductive layer 616 (e.g., constructed as per thermally conductive layer 16 described above) is laminated on the flexible film 650 and has an adhesive surface 616A (e.g., constructed as per adhesive surface 16A described above) on a skin-contacting side. While not shown, a removable release liner may be disposed on the adhesive surface 616A for selective removal when pad 610 is used. Further, fluid circulation inlet/outlet ports and tubes and overall system flow arrangements may be utilized as per the other described embodiments.

The flexible base member 618 may comprise a thermal-molded polymer material such as polyethylene, polyeurathane, polyvinyl chloride, and most preferably, ethylene-vinyl acetate copolymers. The material may be provided in the form of an insulating, closed cell foam having a density of about 2 to 12 lb/ft$^3$. By way of example, the fabrication process for base member 618 may comprise injection molding, vacuum forming or compression molding. The insulating capability may be as per insulating layer 18 described above.

The configuration and pattern of dimples 624 should accommodate flexibility of pad 610 in its final construction. As will be appreciated, flexibility is desirable as the pad 610 should conform to the irregular surface of a patient's skin while avoiding the creation of high stress points. In this regard, pad 610 should accommodate flexure wherein the adhesive surface 616A is disposed in a concave orientation to contact the skin of a patient, and wherein film layer 652 may readily buckle between adjacent dimples 624 upon such flexure.

Figure 9B:
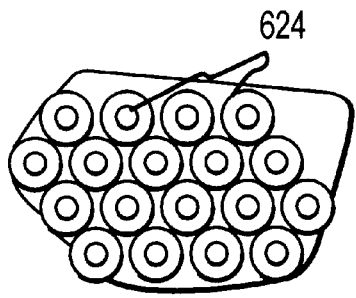
FIGS. 9A and 9B, 10A and 10B, and 11A and 11B illustrate partial side and top views of three different dimple patterns employable in different embodiments of medical pads in accordance with the present invention.
Figure 9A:
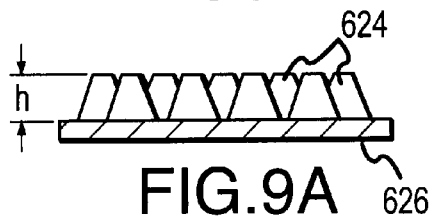

As noted above a number of dimple configurations and patterns may be utilized. As shown in FIG. 8, and FIGS. 9A, 9B, dimples 624 may be of a truncated cone configuration, with adjacent rows and adjacent columns staggered 60° to provide a high dimple density to support film layer 650, yet accommodate the buckling of film layer 650 therebetween during flexure. While the sidewalls of dimples 624 may be of a variety of configurations (e.g., perpendicular or tapered relative to back surface layer 626), angled sidewalls are advantageous since they tend to discourage the formation of a stagnant boundary layer in the circulated fluid. Further, angled walls facilitate removal of base member 618 from a forming mold during production and tend to define a thicker average layer of thermal insulation on the outward facing side of base member 618. Preferably, for optimal production and performance, the height h of dimples 624 is within the range of 0.02 to 0.2 inches, and most preferably, within the range of 0.04 to 0.10 inches.

Figure 10B:
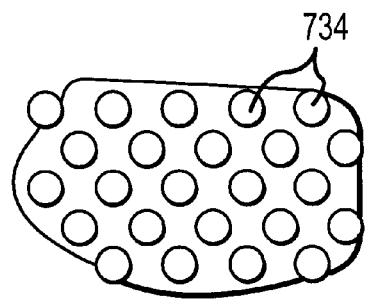
Figure 10A:
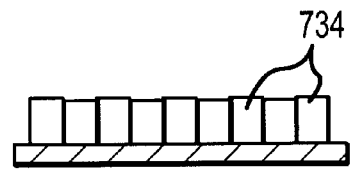
Figure 11B:
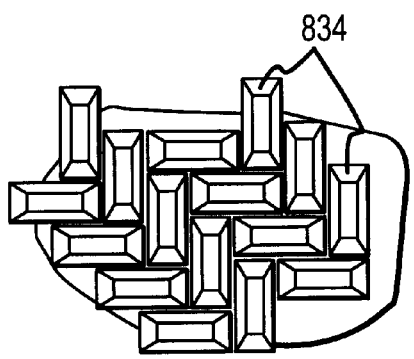
Figure 11A:
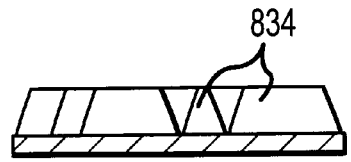

FIGS. 10A, 10B and 11A, 11B illustrate two alternate dimple configurations and patterns. In particular. FIGS. 10A and 10B illustrate cylindrical dimples 734 arranged in rows and columns that are spaced and offset 60°. In the arrangement of FIGS. 11A and 11B, elongated, truncated, pyramidal shaped dimples 834 are disposed in a herringbone pattern. Such an arrangement may yield further fluid flow and moldability advantages.

Figure 12B:
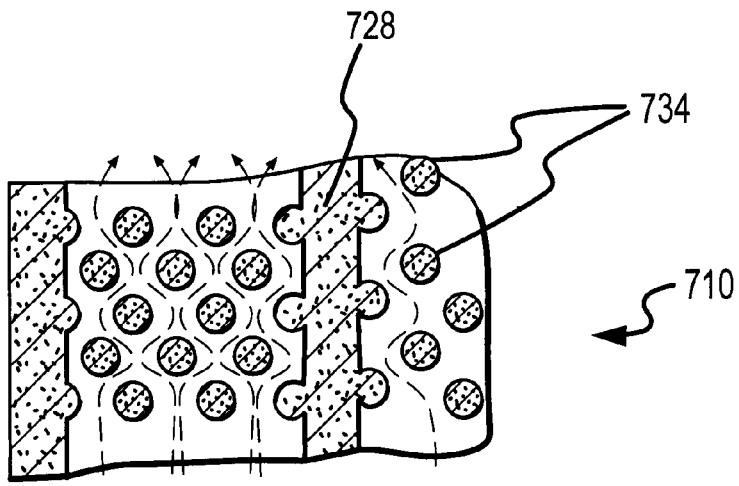
FIGS. 12A and 12B illustrate a partial side cross-sectional view and top cross-sectional view (i.e., taken along cross-section line BB of FIG. 12A), respectively, of the medical pad embodiment of FIGS. 10A and 10B.
Figure 12A:
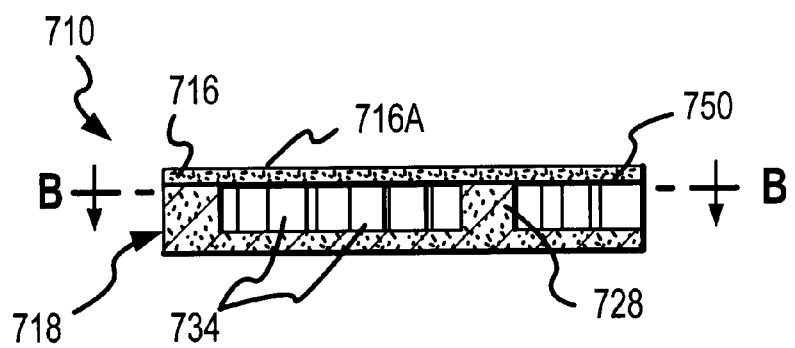
Figure 12C:
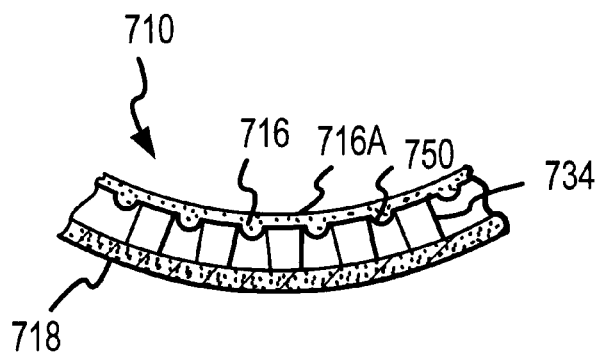
FIG. 12C illustrates a partial side cross-sectional view of the embodiment of FIG. 12C in a flexed state.

FIGS. 12A–12C illustrate an arrangement corresponding with FIGS. 10A and 10B in which cylindrical dimples 734 are utilized in yet another embodiment of a medical pad 710. As shown, medical pad 710 may include a base member 718 integrally formed to define dimples 734 and rib members 728. Film layer 750 may be welded to the base member 718, including interconnection about the peripheries thereof. A thermally conductive layer 716 may be provided with an adhesive surface 716A. As shown in FIG. 12B, tortuous fluid pathways are defined between the dimples 734 and ribs 728. As further shown by FIG. 12C, a medical pad 710 may flex into a concave configuration towards adhesive surface 716A to enhance contact and thermal transfer with a patient's skin. For such purposes, film layer 752 is disposed to readily buckle between adjacent dimples 734.

Figure 13:
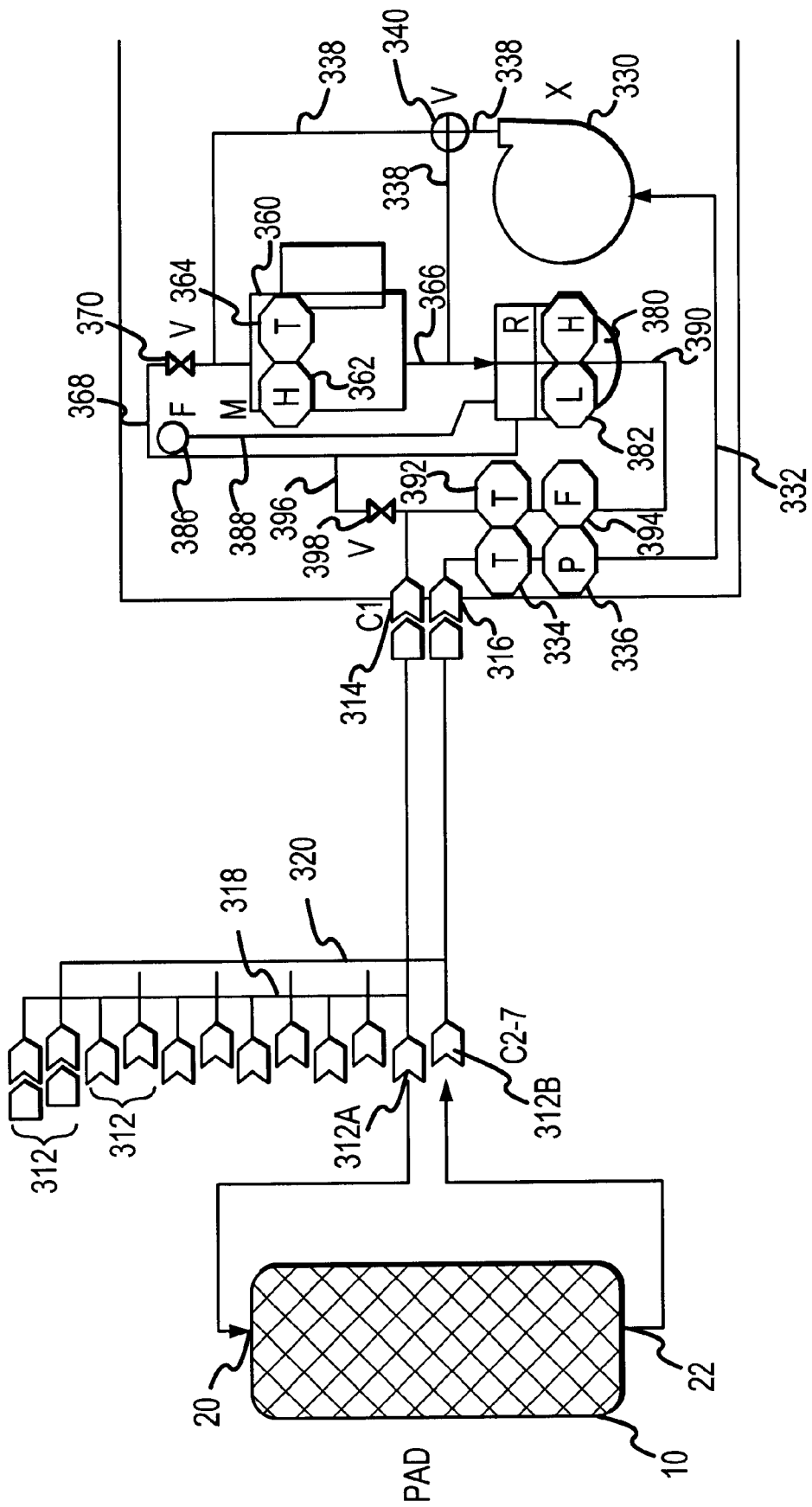
FIG. 13 illustrates a schematic diagram of one embodiment of a medical pad and a related fluid circulating system in accordance with the present invention.

Referring, now to FIG. 13, a schematic diagram of one embodiment of a fluid circulating system 310 is shown connected with a medical pad such as the pad 10 described in the preceding text. It should be appreciated that the fluid circulating system 310 may also be used with the pads 110, 210 shown in FIGS. 5–6 and 6–7, as well as any pad constructed in accordance with the present invention. The fluid circulating system 310 includes a plurality of pad connector pairs 312. Each connector pair 312 includes an inlet connector 312A for connection, via a length of flexible tubing or the like, with the inlet 20 of the pad 10 and an outlet connector 312B for connection, via a length of flexible tubing or the like, with the outlet 22 of the pad 10. In the embodiment shown, the fluid circulating system includes six pad connector pairs 312 thereby permitting connection of six pads 10 with the fluid circulating system 310. However, it should be appreciated that there may be fewer or more pad connector pairs 312. Each inlet connector 312A of the pad connector pairs 312 is connected via an inlet feeder line 318 to a main inlet connector 314, and each outlet connector 312B of the pad connector pairs 312 is connected via an outlet feeder line 320 to a main outlet connector 316. The fluid circulating system 310 also includes a pump 330, a temperature storage module 360, and a fluid reservoir 380.

The pump 330 is connected downstream via a pump inlet line 332 from the main outlet connector 316 and is preferably self-priming. A temperature sensor 334 and a pressure sensor 336 in the pump inlet line 332 measure the temperature and pressure, respectively, of the fluid exiting the pad 10 or pads connected to the fluid circulating system 310. Information from the pressure sensor 336 may be used in controlling the speed of the pump 330 so that generally constant negative pressure is maintained The pump 330 is connected upstream via pump outlet lines 338 and a three-way valve 340 with both the reservoir 380 and the temperature storage module 360.

The temperature storage module 360 includes cooling/heating elements 362 and a temperature sensor 364. The cooling/heating elements 362 may be activated to cool/heat fluid within the temperature storage module 360 to a desired temperature detectable by the temperature sensor 364. The temperature storage module 360 is connected via a primary temperature storage module outlet line 366 upstream from the reservoir 380 so that fluid which has been cooled/heated to a desired temperature within the temperature storage module 360 flows therefrom to the reservoir 380 while the pump 330 is operating (i.e pumping fluid therethrough). The three-way valve 340 may be regulated to control the proportion of fluid 14 that flows to the reservoir 380 directly from the pump 330 and the portion of fluid 14 that flows from the pump 330 through the temperature storage module 360 to the reservoir 380 in order to control the temperature of the fluid flowing into the pad 10. The temperature storage module 360 is also connected via a secondary temperature storage module outlet line 368 line to the reservoir 380. A normally open valve 370 in the secondary temperature storage module outlet line 368 permits fluid to drain from the temperature storage module 360 to the reservoir 380 when the pump 330 is not operating.

The fluid reservoir 380 includes a level sensor 382 for detecting the level of fluid within the reservoir 380 and cooling/heating elements 384 for pre-cooling/pre-heating liquid within the reservoir 380. When desirable (e.g. when the level sensor 382 indicates that the fluid level has fallen below a specified level), additional fluid may be added to the reservoir through a fill port 386 that is connected to the reservoir 380 by a fill line 388. Preferably, the reservoir 380 has a non-mixing inlet and outlet in order to minimize cooling of fluid within the reservoir 380. The outlet of the reservoir 380 is connected via a reservoir outlet line 390 to the main inlet connector 314. A temperature sensor 392 and a flow sensor 394 are provided in the reservoir outlet line 390. The temperature sensor 392 measures the temperature of fluid provided to the pad inlets via the inlet feeder line 318. Information from the temperature sensor 392 may be utilized in regulating the three-way valve 340 to control the fluid temperature. Information from the flow sensor 394 and the temperature sensor 334 in the pump inlet line 332 may be utilized in determining the heat transfer between the patient and pads connected to the fluid circulating system 310. A drain line 396 with a normally closed two-way valve 398 is provided for draining the pads to the reservoir 380 when the cooling/heating procedure is completed.

Figure 14:
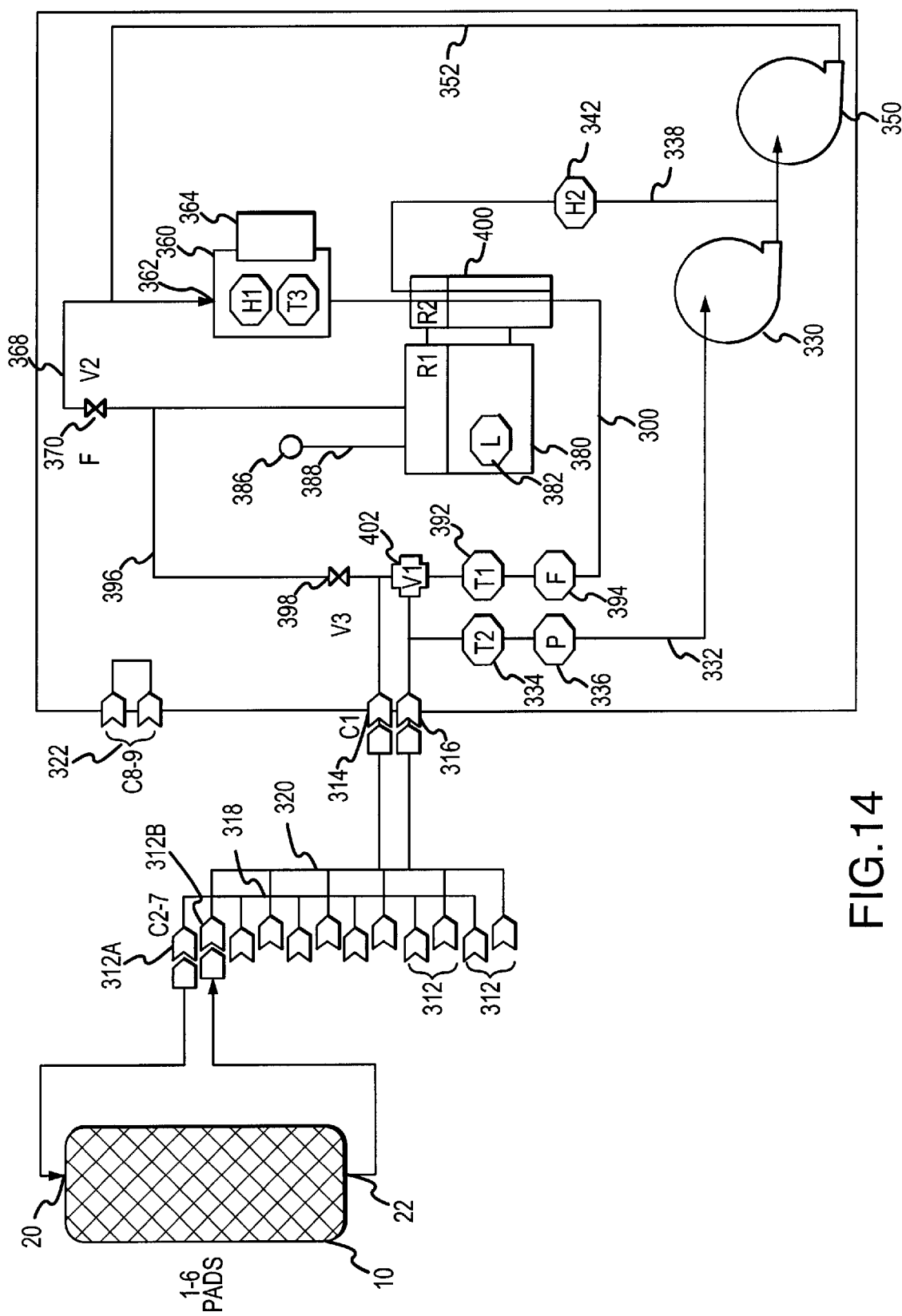
FIG. 14 illustrates a schematic diagram of another embodiment of a medical pad and a related fluid circulating system in accordance with the present invention.

In FIG. 14 a schematic diagram of another embodiment of a fluid circulating system 310' is shown. The fluid circulating system 310' is similar to the system 310 shown in FIG. 13 and like elements are referenced with the same numbers. The fluid circulating system 310' includes a plurality of pad connector pairs 312, each having an inlet connector 312A and an outlet connector 312B. In the embodiment shown, the fluid circulating system includes six pad connector pairs 312 thereby permitting connection of six pads 10 with the fluid circulating system 310'. However, it should be appreciated that there may be fewer or more pad connector pairs 312. Each inlet connector 312A of the pad connector pairs 312 is connected via an inlet feeder line 318 to a main inlet connector 314, and each outlet connector 312B of the pad connector pairs 312 is connected via an outlet feeder line 320 to a main outlet connector 316. The fluid circulating system 310' also includes first and second pumps 330, 350, a temperature storage module 360, and first and second fluid reservoirs 380, 400. An additional connector pair 322 may be included for attachment of a pad and recirculation during bypass.

The pump first 330 is connected downstream via a pump inlet line 332 from the main outlet connector 316 and is preferably self-priming. A temperature sensor 334 and a pressure sensor 336 are disposed in the pump inlet line 332. The first pump 330 is connected upstream via first pump outlet lines 338 with both the second reservoir 400 and the second pump 350. A cooling/heating element 342 is disposed in the outlet line 338 between the first pump 330 and the second reservoir 400 for in-line cooling/heating of the fluid circulated through the system 310'. The second pump 350 is connected downstream from the first pump 330 and is connected upstream via a second pump outlet line 352 to the temperature storage module 360. The second pump 360 is preferably self-priming and recirculates fluid through the temperature storage module 360 for purposes of temperature control.

The temperature storage module 360 includes cooling/heating elements 362 and a temperature sensor 364. The cooling/heating elements 362 may be activated to cool/heat fluid within the temperature storage module 360 to a desired temperature detectable by the temperature sensor 364. The temperature storage module 360 is connected via a primary temperature storage module outlet line 366 upstream from the second reservoir 400 so that fluid which has been cooled/heated to a desired temperature within the temperature storage module 360 may flow therefrom to the second reservoir 400. The temperature storage module 360 is also connected via a secondary temperature storage module outlet line 368 line to the first reservoir 380. A normally open valve 370 in the secondary temperature storage module outlet line 368 permits fluid to drain from the temperature storage module 360 to the first reservoir 380 when the second pump 350 is not operating.

The first fluid reservoir 380 includes a level sensor 382 for detecting the level of fluid within the reservoir 380. When desirable (e.g. when the level sensor 382 indicates that the fluid level has fallen below a specified level), additional fluid may be added to the first reservoir through a fill port 386 that is connected to the reservoir 380 by a fill line 388. The first reservoir 380 is connected for fluid flow therebetween with the second reservoir 400. The second reservoir 400 functions as a recirculating reservoir receiving fluid from the first pump 330 and the temperature storage module 360 and providing fluid via a reservoir outlet line 390 to the main inlet connector 314. When necessary, additional fluid may be provided from the first reservoir 380 to the second reservoir. Using two reservoirs instead of just one reservoir as with the system 310 in FIG. 13 prevents significant mixing of recirculated fluid that has been cooled/heated with the fluid supply maintained in the first reservoir 380. A temperature sensor 392 and a flow sensor 394 are provided in the reservoir outlet line 390, as well as a three-way valve 402. The three-way valve 402 connects the main outlet connector 316 with the reservoir outlet line 390. The three-way valve normally bypasses the main outlet connector 3160 so that fluid flows to the main inlet connector 314 from the second reservoir 400 via the reservoir outlet line 390. A drain line 396 with a normally closed two-way valve 398 is provided for draining the pads to the first reservoir 380 when the cooling/heating procedure is completed.

Figure 15:
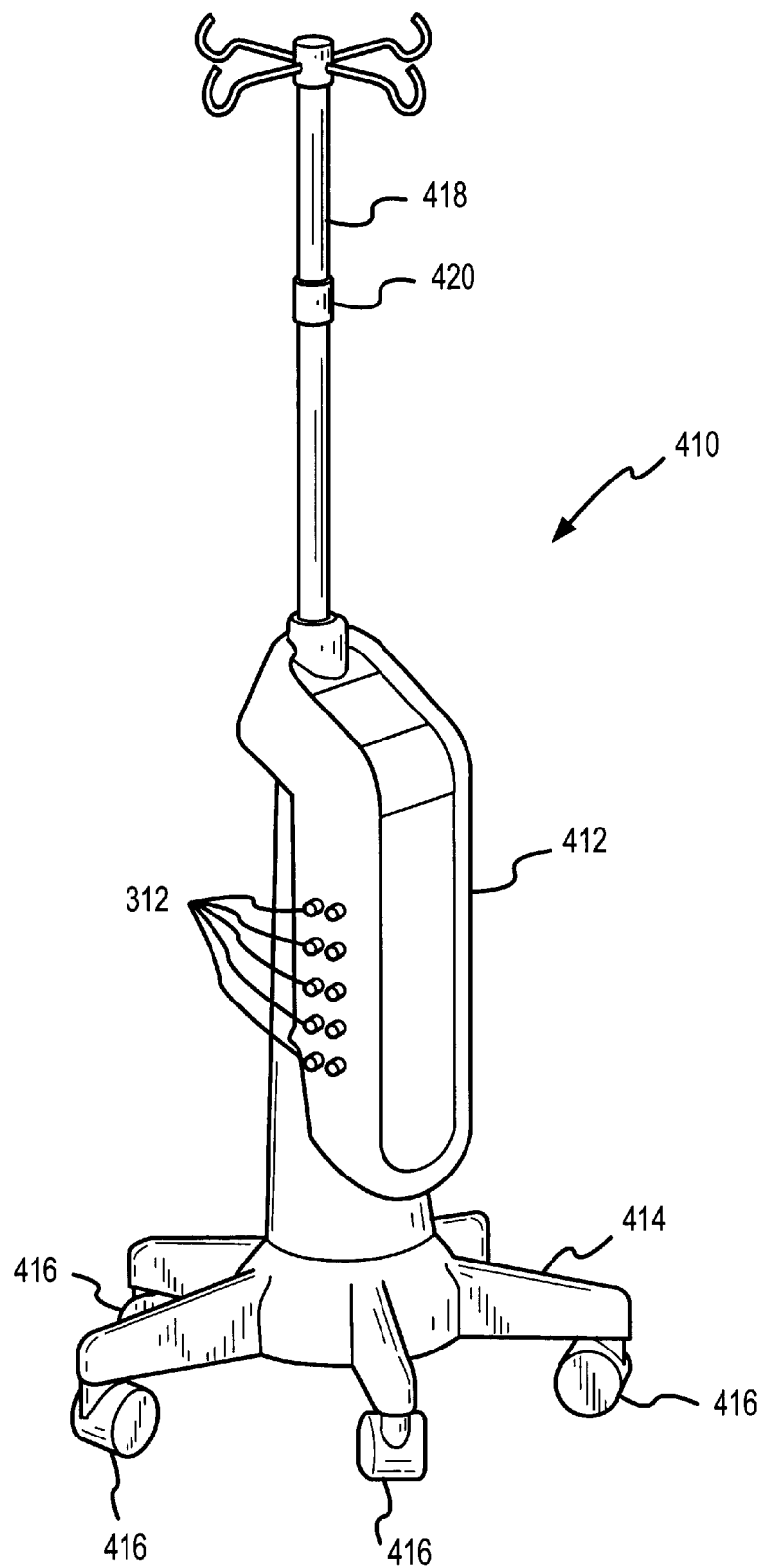
FIG. 15 illustrates a perspective view of one embodiment of a cooler/heater console system including a fluid circulating system as depicted in FIG. 13.

Referring now to FIG. 15, a fluid circulating system such as the systems 310, 310' depicted in FIGS. 8 and 9 may be included within a portable cooler/heater console 410. The console 410 includes a housing 412, a base 414 with casters 416 and an extendable hangar stand 418. The housing 412 contains the components of the fluid circulating system 310, 310'. The pad connector pairs 312 for connecting pads to the fluid circulating system 310 are preferably located on one side of the housing 412. The casters 416 facilitate moving the console 410 adjacent to an operating table or the like when needed and also facilitate moving the console 410 in conjunction with moving a patient having one or more pads adhered thereto. The extendable hangar stand 418 provides a convenient means for hanging intravenous solutions and infusion pumps. The hangar stand 418 may be adjusted to an appropriate height by loosening retention collar 420, moving the hangar stand 418 up or down as necessary, then re-tightening the retention collar 420.

A medical pad and related fluid circulating system such as the pad 10 and system 310 described above may be utilized in the following manner to both cool and rewarm a patient. One or more pads 10 of appropriate configurations are selected. The pads 10 are adhered to the skin of the patient at appropriate locations (e.g. on the patient's torso, thighs and neck) by bringing the adhesive surface 16A of the pads 10 into contact with the patient's skin. The inlet 20 and outlet 22 of the pads 10 are connected to respective pad connector pairs 312 of the fluid circulating system 310. The pump 330 is operated to draw fluid at an appropriate temperature below that of the patient from the reservoir 380 through the fluid containing layer 12. The appropriate temperature may be achieved by regulating the three-way valve 340 and operating the cooling/heating elements 362, 384 as necessary. Thermal energy from the patient is absorbed by the circulated fluid thereby cooling the patient. Once the patient has reached the desired body temperature (e.g. 2–3° C. below normal when treating a stroke or head trauma patient), the patient's lowered body temperature may be maintained by continuing to circulate fluid at an appropriate temperature through the pads 10. When the patient needs to be rewarmed, fluid at an appropriate temperature above that of the patient may be circulated through the pads 10 thereby releasing thermal energy to the patient.

In operation, the level of fluid in the fluid reservoir 380 should be maintained at or below the level of the patient so that the pad is under negative pressure even when fluid flow stops.

Figure 16:
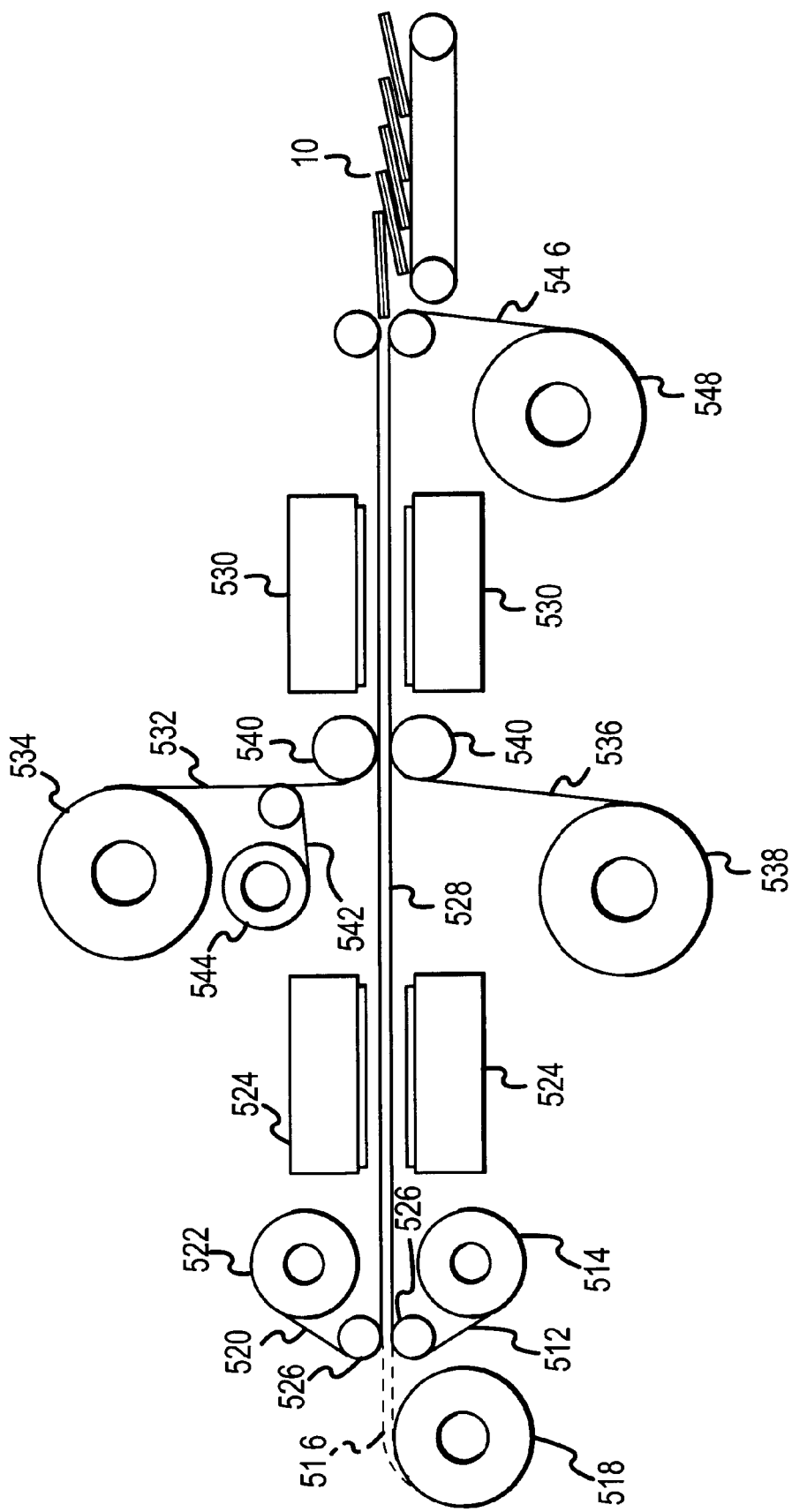
FIG. 16 illustrates schematic view of a manufacturing line for manufacturing a medical pad in accordance with the present invention.

Referring now to FIG. 16, a schematic view of a manufacturing line 510 for manufacturing a medical pad such as the pad 10 described above is shown. A first layer of film material 512 from a lower film supply roll 514, netting 516 from a netting supply roll 518, a second layer of film material 520 from an upper film supply roll 522 are drawn into a heated die 524. The first and second layers of film material 312, 320 preferably have a thermally reactive adhesive coated on their respective sides facing the netting 516. Preferably, the adhesive coated on the layers of film material 512, 520 has an adhesive application temperature in the range of 210–230° F. In this regard, the first and second layers of film material 512, 520 may be a polypropylene film with a copolymer adhesive such as Trans-kote OPP/MR manufactured by Transilwrap Company, Inc. of Chicago, Ill. A pair of pinch rollers 526 pinch the first layer of film 512, netting 516 and second layer of film 520 together to form a sandwich 528 before they enter the die 524.

The die 524 is heated to an appropriate temperature (e.g. 230° F.) and its surfaces are formed such that when pressed into the sandwich 528, the layers of film 512, 520 are bonded by the thermally reactive adhesive to the netting 516 and to one another in a pattern corresponding to the perimeter edges of the configuration of the pad desired. The netting 516 is also melted in by the die 524 along the perimeter edges and in internal lines to form water flow channels. The sandwich 528 exits the heated die 524 and is drawn into a die-cut press 530. In conjunction with the sandwich 528, adhesive backed closed cell foam 532 is drawn from a foam supply roll 534 and hydrogel material 536 from a hydrogel supply roll 538 are drawn into the die-cut press 530. Pinch rollers 540 nip roll laminate the foam 532 and hydrogel 538 onto respective sides of the sandwich 528 before entering the die-cut press 530. A release liner 542 over the adhesive surface of the foam 532 may be removed to a waste roll 544 before the foam reaches the pinch rollers 540.

Perimeter and manifold cuts at appropriate locations are performed by the die-cut press 530. The perimeter cuts separate the pads 10 from the waste material 546 which may be removed to a waste roll 548. The manifold cuts extend through only the foam 532 and second layer of film material 520. The manifold cut-out sections may be removed and manifolds 60 bonded to the foam 532 over the cut-out sections to produce finished pads 10.

The foregoing description of the present invention has been provided for purposes of illustration and description. This description is not intended to limit the invention and various modalities thereof. Variations, embodiments and modifications may be apparent to those skilled in the art and are intended to be within the scope of the following claims.

What is claimed is:

1. A medical pad for contacting and exchanging thermal energy with a patient, said pad comprising:
   a flexible upper sheet;
   a flexible base member interconnected to said flexible upper sheet to define a fluid containing layer therebetween, said base member including a plurality of dimples for supporting said flexible upper sheet and for defining tortuous fluid flow paths within said fluid containing layer; and
   an adhesive surface disposed on a skin-contacting side of said flexible upper sheet and adapted for releaseable adhesive contact with skin of a patient.

2. The medical pad of claim 1, wherein said plurality of dimples are arranged in a predetermined pattern of rows and columns.

3. The medical pad of claim 1, wherein said plurality of dimples are of a predetermined configuration selected from a group consisting of: a truncated cone configuration, a cylindrical configuration, and an elongated, truncated pyramid configuration.

4. The medical pad of claim 1, wherein said base member is of a foam construction.

5. The medical pad of claim 4, wherein said base member has a density of between about 2 to 12 lb/ft$^3$.

6. The medical pad of claim 1, wherein said base member comprises at least one material selected from a group consisting of:
   polyethylene;
   polyurethane;
   polyvinyl chloride; and
   ethylene-vinyl acetate copolymers.

7. The medical pad of claim 1, further comprising:
   a conformable, thermally conductive layer laminated to said flexible upper sheet, said thermally conductive layer being disposed between said adhesive surface and said flexible upper sheet.

8. The medical pad of claim 7, wherein said conformable, thermally conductive layer has a thermal transfer rate of at least about 13.33 cal/hr-centimeters$^2$-degree centigrade and comprises a material having an elastic modulus of between about 40 and 1,000 pascals.

9. The medical pad of claim 7, wherein said conformable, thermally conductive layer comprises a hydrogel material.

10. The medical pad of claim 1, wherein said adhesive surface has a peel value against the skin of a patient at initial application of at least about 10 gm/inch.

11. A medical pad for contacting and exchanging thermal energy with a patient, said pad comprising:
    a flexible upper sheet; and
    a flexible base member interconnected to said flexible upper sheet to define a fluid containing layer therebetween, said base member including a plurality of dimples for supporting said flexible upper sheet and for defining tortuous fluid flow paths within said fluid containing layer, wherein said plurality of dimples have a height of between about 0.02 to 0.2 inches.

12. A medical pad for contacting and exchanging thermal energy with a patient, said pad comprising:

a flexible upper sheet;

a flexible base member interconnected to said flexible upper sheet to define a fluid containing layer therebetween, said base member including a plurality of dimples for supporting said flexible upper sheet and for defining tortuous fluid flow paths within said fluid containing layer; and at least one rib member extending laterally between a portion of adjacent ones of said plurality of dimples to further define said tortuous fluid flow paths within said fluid containing layer.

13. The medical pad of claim 12, wherein said base member is formed to integrally define said plurality of dimples and said at least one rib member.

14. A medical pad for contacting and exchanging thermal energy with a patient, said pad comprising:

a flexible base member of foam construction having a plurality of integrally defined dimples;

a flexible film interconnected to said flexible base member to define a fluid containing layer therebetween, wherein said plurality of dimples of said flexible base member define tortuous fluid flow paths within said fluid containing layer;

a thermally conductive layer laminated to one side of said flexible film; and an adhesive surface disposed on said thermally conductive layer and adapted for releaseable adhesive contact with skin of a patient.

15. The medical pad of claim 14, wherein said flexible base member further includes a plurality of integrally defined rib members each laterally extending between different adjacent ones of said plurality of dimples.

16. The medical pad of claim 14, wherein said flexible base member comprises at least one material selected from a group consisting of:

polyethylene;

polyurethane;

polyvinyl chloride; and ethylene-vinyl acetate copolymers.

17. The medical pad of claim 14, wherein said thermally conductive layer comprises a liquid suspended in a polymer matrix.

18. The medical pad of claim 14, wherein said plurality of dimples have a height of between about 0.02 to 0.2 inches.

19. The medical pad of claim 14, wherein said plurality of dimples are of a predetermined configuration selected from a group consisting of: a truncated cone configuration, a cylindrical configuration, and an elongated, truncated pyramid configuration.

20. The medical pad of claim 14, wherein said pad is flexible in a concave manner at said adhesive surface, and wherein said flexible film buckles between said plurality of dimples when said medical pad is in a flexed, concave state.

21. A medical pad for contacting and exchanging thermal energy with a patient, said pad comprising:

a flexible upper sheet having a lower smooth surface; and a flexible base member interconnected to said flexible upper sheet to define a fluid containing layer therebetween, said base member including a plurality of dimples provided on an upper surface thereof for supporting said flexible upper sheet and for defining tortuous fluid flow paths within said fluid containing layer, said plurality of dimples being arranged in a predetermined staggered pattern wherein said lower smooth surface of said flexible upper sheet is supported at a plurality of points of contact with said dimples, said dimples being staggered in at least two transverse directions on the upper surface of said base member.

22. The medical pad of claim 21 wherein said dimples are arranged in a predetermined staggered pattern of offset rows and columns.

23. The medical pad of claim 22 wherein said dimples within adjacent said rows and adjacent said columns are offset from one another by sixty degrees.

24. The medical pad of claim 21 wherein said dimples are arranged in a herringbone pattern.

25. The medical pad of claim 21 wherein said base member is formed to integrally define said plurality of dimples.

\* \* \* \* \*